United States Patent
Sabharwal et al.

(10) Patent No.: US 11,931,341 B2
(45) Date of Patent: Mar. 19, 2024

(54) COMPOSITIONS AND METHODS FOR THE TREATMENT AND PREVENTION OF MUSCULAR DYSTROPHY

(71) Applicant: University of Iowa Research Foundation, Iowa City, IA (US)

(72) Inventors: Rasna Sabharwal, Iowa City, IA (US); Robert Weiss, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 17/040,368

(22) PCT Filed: Mar. 22, 2019

(86) PCT No.: PCT/US2019/023644
§ 371 (c)(1),
(2) Date: Sep. 22, 2020

(87) PCT Pub. No.: WO2019/183513
PCT Pub. Date: Sep. 26, 2019

(65) Prior Publication Data
US 2021/0023057 A1    Jan. 28, 2021

Related U.S. Application Data

(60) Provisional application No. 62/646,701, filed on Mar. 22, 2018.

(51) Int. Cl.
*A61K 31/4178* (2006.01)
*A61K 9/00* (2006.01)
*A61K 45/06* (2006.01)

(52) U.S. Cl.
CPC ........ *A61K 31/4178* (2013.01); *A61K 9/0019* (2013.01); *A61K 9/0043* (2013.01); *A61K 9/0053* (2013.01); *A61K 45/06* (2013.01)

(58) Field of Classification Search
CPC .................................................. A61K 31/4178
See application file for complete search history.

(56) References Cited

U.S. PATENT DOCUMENTS

| | | | |
|---|---|---|---|
| 7,652,054 B2 * | 1/2010 | Alterman | A61P 43/00 548/346.1 |
| 2012/0035232 A1 | 2/2012 | Steckelings et al. | |
| 2016/0175286 A1 | 6/2016 | Springer et al. | |

FOREIGN PATENT DOCUMENTS

WO    2015189342 A1    12/2015

OTHER PUBLICATIONS

Accorsi et al., Human Molecular Genetics, 2016, 25(21): 4624-4634.*
Martinez et al., American Journal of Medical Genetics, 2011, Part A, 155(12): 3025-3029.*

* cited by examiner

*Primary Examiner* — Rei Tsang Shiao
(74) *Attorney, Agent, or Firm* — Dentons Davis Brown, PC; Matthew Coryell

(57) ABSTRACT

The present invention relates to a new use of compounds that are angiotensin II (Ang II) agonists, more particularly agonists of the Ang II type 2 receptor (the AT2 receptor), and especially agonists that bind selectively to the AT2 receptor, for the prevention or treatment of muscular dystrophy or complications associated with muscular dystrophy.

20 Claims, 3 Drawing Sheets

COMPOSITIONS AND METHODS FOR THE TREATMENT AND PREVENTION OF MUSCULAR DYSTROPHY

CROSS-REFERENCE TO RELATED APPLICATION(S)

This application is the National Stage of International Application No. PCT/US2019/23644, filed Mar. 22, 2019, which claims the benefit of U.S. Provisional Application No. 62/646,701, filed on Mar. 22, 2018; each of which is incorporated herein by reference in its entirety.

FIELD OF THE INVENTION

This invention relates to a new use of compounds that are angiotensin II (Ang II) receptor agonists, more particularly selective agonists of the Ang II type 2 receptor (hereinafter the AT2 receptor), and especially agonists that bind selectively to that receptor, for prevention and treatment of muscular dystrophy.

BACKGROUND OF THE INVENTION

Muscular dystrophies (MDs) have clinical features of muscle disease such as muscle weakness with connected disabilities and dystrophic muscle, which stems from a diverse group of diseases that can be separated into sub-categories e.g. dystrophinopathies (Duchenne muscular dystrophy (DMD) and Becker MD), myotonic dystrophy, limb girdle muscular dystrophies (LGMD), Emery-Dreifuss muscular dystrophies, facioscapulohumeral muscular dystrophy, oculopharyngeal muscular dystrophy, and congenital muscular dystrophies.

The most common (1 in approx. 5000 live births) and severe form of MD is Duchenne muscular dystrophy (DMD), which is an x-linked recessive disease with defects or absence of sarcolemmal protein dystrophin. Dystrophin is a large cytoskeletal linked protein having a broad extensive participation in general cellular processes and interacts with many other molecules. Dystrophin is thought to stabilize the myofiber membrane during muscle contraction, thus affecting membrane instability, alterations in key ion gradients, and disruption of second messenger pathways connected to the loss of dystrophin.

This progressive neuromuscular condition leads to severe long-term muscle degeneration, presenting itself with a diagnosis at ages 3-7 years, loss of independent mobility in early teen years of age, followed by further sever implications in pulmonary and cardiac dysfunction in early adulthood (Neuromuscular Disorders 27 (2017) 4-14, D'Amario D, et al. Heart 2017; 0:1-10). Better treatments of the cardiac and respiratory complications together with glucocorticoid therapy have improved the situation during the pediatric years. Current therapeutic strategies involve corrections of the genetic mutation(s) that give rise to the disease, but attention is also given to disease-modifying pathways.

With regards to DMD, glucocorticoids are currently the only therapeutic treatment that maintains muscle strength and function in DMD children, and are tolerated fairly well but with significant side effects such as weight gain and slower vertical growth, but also rare and severe side effects such as elevated blood pressure, gastrointestinal lesions etc. Clinical trials to find a new treatment with glucocorticoid benefits, without the side-effects are currently performed on Vamorolone NCT02760264, NCT02760277, NCT03038399), and edasalonexent (CAT-1004, NCT02439216).

Since most DMD patients develop dilated cardiomyopathy, the use of various cardioprotective therapies have been employed, using for example ACE inhibitors, beta-blockers, angiotensin blockers, and aldosterone agonists, which seems to improve or preserve left ventricular systolic function, and delay the progression of cardiomyopathy.

The angiotensin converting enzyme (ACE) inhibitor lisinopril was compared to the angiotensin II type 1 receptor blocker losartan in a randomized, double-blind trial, resulting in after 1 year similar improvement in DMD cardiomyopathy (Allen et al. 2013).

Table 4 of Dowling et al. (Am J Med Genet. 2017; 1-38) gives an extensive and recent summary of the therapeutic strategies for DMD.

LGMDs are clinically heterogeneous, and genetically diverse and in pediatrics the major subtypes are sarcoglycanopathies (gene mutations in the sarcoglycan membrane protein complex presenting itself similar to DMD), dystroglycanopathies and calpainopathies. Conditions of LGMD are presented after the first year of life with limb girdle pattern of weakness, elevated CK levels, and dystrophic biopsies, and usually progressive weakness. Studies in mouse models of sarcoglycanopathy suggest steroids could be deleterious, particularly to cardiac function (Bauer, Macgowan, Blain, Bushby, & Straub, 2008), and at present there are no recommendations to consider steroids in LGMD patients. Modification of the TGF pathway (either genetically or pharmacologically with ACE inhibitors) has been demonstrated to ameliorate the dystrophic phenotype (Accornero et al., 2014; Goldstein et al., 2014) in models of both DMD and sarcoglycanopathy. As with many neuromuscular diseases including certain types of LGMD subtypes (Bengtsson, Seto, Hall, Chamberlain, & Odom, 2016), gene therapy could be of significant importance and there are ongoing clinical trials.

There remains a need to identify new and effective treatments and preventative therapies for muscular dystrophy and complications associated therewith.

The listing or discussion of an apparently prior-published document in this specification should not necessarily be taken as an acknowledgement that the document is part of the state of the art or is common general knowledge.

BRIEF SUMMARY OF THE INVENTION

Disclosed herein is a method of treating or preventing muscular dystrophy or complications associated with muscular dystrophy in a subject in need thereof, comprising administering to the subject a therapeutically effective amount of an AT2 receptor agonist or a pharmaceutically acceptable salt, solvate or prodrug thereof. In certain aspects, the AT2 receptor agonist is a selective agonist of an AT2 receptor. According to certain implementations of these aspects, the selective agonist of an AT2 receptor is a non-peptide selective agonist. In exemplary embodiments, the AT2 receptor agonist is N-butyloxycarbonyl-3-(4-imidazol-1-ylmethylphenyl)-5-iso-butylthiophene-2-sulfonamide (C21) or a pharmaceutically acceptable salt (preferably an HCl salt), a solvate or a prodrug thereof.

Further disclosed herein is AT2 receptor agonist, or a pharmaceutically acceptable salt, solvate or prodrug thereof, for use in treating or preventing muscular dystrophy or complications associated with muscular dystrophy.

Still further disclosed herein is the use of an AT2 receptor agonist, or a pharmaceutically acceptable salt, solvate or prodrug thereof, in the manufacture of a medicament for treating or preventing muscular dystrophy or complications associated with muscular dystrophy.

According to certain embodiments, the disclosed methods and/or disclosed compositions are useful in the treatment of muscular dystrophy, including the treatment of Duchenne muscular dystrophy, myotonic dystrophy, facioscapulohumeral muscular dystrophy, Becker muscular dystrophy, limb-girdle muscular dystrophy, oculopharyngeal muscular dystrophy, and Emery-Dreifuss muscular dystrophy.

According to further embodiments, the disclosed methods and/or disclosed compositions are useful in the treatment of, or prevention of, one or more complications associated with muscular dystrophy including muscle weakness, progressive muscular wasting, muscle spasms, reduced ambulation, myopathic gait, poor balance, scoliosis, cardiomyopathy, cardiac disease, respiratory difficulty and respiratory disease.

According to still further embodiments the disclosed methods and/or disclosed compositions reduces cardiac dysfunction and/or improves heart function in a subject suffering from muscular dystrophy.

In still further aspects, the disclosed methods and/or disclosed compositions treats or prevents limb-girdle muscular dystrophy, muscle weakness associated with limb-girdle muscular dystrophy or cardiopulmonary complications associated with limb-girdle muscular dystrophy.

In certain aspects, the administration comprises the introduction of the AT2 receptor agonist, or pharmaceutically acceptable salt, solvate or prodrug thereof, into the subject nasally, orally, or parenterally.

In still further aspects, the AT2 receptor agonist, or pharmaceutically acceptable salt, solvate or prodrug thereof, is administered to a subject at a dose of from about 1 to about 1000 mg per day.

In yet further aspects, the AT2 receptor agonist, or pharmaceutically acceptable salt, solvate or prodrug thereof, is administered in combination with an AT1 receptor antagonist. In expemplary emobodiements of these aspects, the AT1 receptor antagonist is selected from the group consisting of losartan, azilsartan, candesartan, eprosartan, fimasartan, irbesartan, milfasartan, olmesartan, pomisartan, pratosartan, ripiasartan, saprisartan, tasosartan, telmisartan, valsartan and combinations thereof.

Accord to still further aspects, the AT2 receptor agonist, or pharmaceutically acceptable salt, solvate or prodrug thereof, is administered in combination with an inhibitor of angiotensin converting enzyme (ACE). In exemplary emobodiments of these aspects, the angiotensin converting enzyme (ACE) inhibitor is selected from the group consisting of captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and combinations thereof.

BRIEF DESCRIPTION OF THE DRAWINGS

The appended drawings are provided to illustrate various aspects of the present inventive concept and are not intended to limit the scope of the present invention unless specified herein.

DETAILED DESCRIPTION

Figure 1:
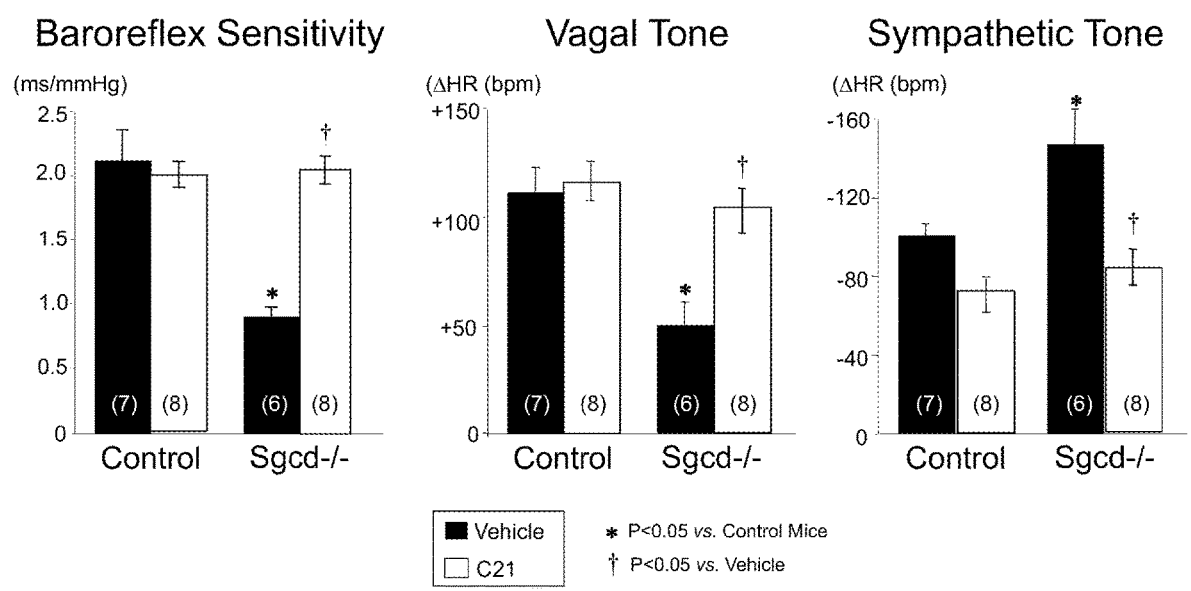
FIG. 1 shows the effects of C21 on baroreflex sensitivity, vagal tone and sympathetic tone compared to control in a δSgcd−/− mouse model (a genetically modified model to imitate limb-girdle muscular dystrophy (LGMD)).

In a first aspect of the invention, there is provided, a method of treating or preventing muscular dystrophy or complications associated with muscular dystrophy in a subject in need thereof comprising administering to the subject a therapeutically effective amount of an angiotensin II type 2 (AT2) receptor agonist or a pharmaceutically acceptable salt, solvate or prodrug thereof. As described herein, such AT2 receptor agonists include compounds that fully or partially active AT2 receptors or stimulate or activate AT2 receptors, and these compounds are referred to herein as the "compounds of the invention".

In a second aspect of the invention, there is provided a compound of the invention (i.e. an AT2 receptor agonist, or a pharmaceutically acceptable salt, solvate or prodrug thereof), for use in treating or preventing muscular dystrophy or complications associated with muscular dystrophy.

In a third aspect of the invention, there is provided the use of a compound of the invention (i.e. an AT2 receptor agonist, or a pharmaceutically acceptable salt, solvate or prodrug thereof) in the manufacture of a medicament for treating or preventing muscular dystrophy or complications associated with muscular dystrophy.

References herein to "methods of the invention" and the like are intended to refer also to the compound for use of the second aspect as well as the use of the third aspect.

The foregoing and other aspects of the present invention will now be described in more detail with respect to the description and methodologies provided herein. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

Compounds that are useful in the aspects of the invention mentioned hereinbefore are agonists of Ang II receptor, more particularly, are agonists of the AT2 receptor. Particular compounds that may be mentioned in this respect are selective agonists of the AT2 sub-receptor, such as non-peptide selective agonists. In some embodiments, the useful compounds are those that fully and those that partially activate the AT2 receptor and those compounds that can stimulate or activate the AT2 receptor. In some embodiments, the compound of the invention (i.e. the AT2 receptor agonist) may be defined as any compound that can stimulate or activate the AT2 receptor. In each embodiment, the compound of the invention may be provided in the form of a pharmaceutically acceptable salt, solvate or prodrug.

As described herein, compounds of the invention can be used for the prevention or treatment of muscular dystrophy. Alternatively, or additionally, they may be used for the prevention or treatment complications associated with muscular dystrophy. In some embodiments, the compound of the invention is N-butyloxycarbonyl-3-(4-imidazol-1-ylmethylphenyl)-5-iso-butylthiophene-2-sulfonamide (Compound 21 or, in short, C21), or a pharmaceutically acceptable salt, solvate or prodrug thereof. A particular salt of C21 that may be mentioned is the HCl salt.

In one embodiment of the method of the present invention, there is provided a method for treating muscular dystrophy or treating or preventing complications associated with muscular dystrophy, which method comprises administration of a therapeutically effective amount of a compound of the invention (or a pharmaceutically acceptable salt, solvate or prodrug thereof) to a subject suffering from muscular dystrophy.

Preferences and options for a given aspect, embodiment, feature or parameter of the invention should, unless the context indicates otherwise, be regarded as having been disclosed in combination with any and all embodiments, preferences and options for all other aspects, embodiments, features and parameters of the invention. For example, many of the aspects, embodiments and features associated with a pharmaceutical formulation may equally apply to a compound of the invention, and vice versa.

The terminology used in the description of the invention herein is for the purpose of describing particular embodiments only and is not intended to limit the scope of the claims. As used in the description of the embodiments of the invention, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about", as used herein when referring to a measurable value such as an amount of a compound, dose, time, temperature, and the like, refers to variations of 20%, 10%, 5%, 1%, 0.5%, or even 0.1% of the specified amount. When a range is employed (e.g., a range from x to y) it is meant that the measurable value is a range from about x to about y, or any range or value therein including x and y, such as about x1 to about y1, etc. It will be further understood that the terms "comprises" and/or "comprising", when used in this specification, specify the presence of stated features, integers, steps, operations, elements, components and/or groups, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

"Effective amount" as used herein refers to an amount of a compound, composition and/or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one skilled in the art by reference to the pertinent texts and literature and/or by using routine experimentation.

By the term "treat", "treating", or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. The terms "treatment", "treat", and "treating" may also refer to reversing, alleviating, inhibiting the progress of a disease or disorder (or a symptom thereof) as described herein, or delaying, eliminating or reducing the incidence or onset of a disorder or disease as described herein, as compared to that which would occur in the absence of the measure taken. The terms "prophylaxis" or "prophylactic use" and "prophylactic treatment" as used herein, refer to any medical or public health procedure whose purpose is to prevent the disease herein disclosed. As used herein, the terms "prevent", "prevention" and "preventing" refer to the reduction in the risk of acquiring or developing a given condition, or the reduction or inhibition of the recurrence of said condition in a subject who is not ill.

A "therapeutically effective" amount as used herein is an amount that is sufficient to treat or prevent (as defined herein) the subject. Those skilled in the art will appreciate that the therapeutic effects need not be complete or curative, as long as some benefit is provided to the subject.

A "subject in need" of the methods of the invention can be a subject known to have or suspected of having muscular dystrophy or complications associated therewith, or a subject that is at risk of having muscular dystrophy or complications associated therewith.

The term "concomitant administration" or "combination administration" of a compound, therapeutic agent or known drug with a compound of the present invention means administration of a known medication or drug and, in addition, the one or more compounds of the invention to the same subject at such time that both the known drug and the compound will have a therapeutic effect. In some cases this therapeutic effect will be synergistic. Such concomitant administration can involve concurrent (i.e., at the same time), prior, or subsequent administration of the known drug with respect to the administration of a compound of the present invention. A person skilled in the art would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described herein, or their pharmaceutically acceptable salts, solvates or prodrugs, for manufacturing a medicament for the purpose of providing for prevention and treatment of muscular dystrophy.

All patents, patent applications and publications referred to herein are incorporated by reference in their entirety. In the event of conflicting terminology, the present specification is controlling. Further, the embodiments described in one aspect of the present invention are not limited to the aspect described. The embodiments may also be applied to a different aspect of the invention as long as the embodiments do not prevent these aspects of the invention from operating for their intended purpose.

Without wishing to be bound by theory, it is thought that renin, a protease, cleaves its only known substrate (angiotensinogen) to form angiotensin I, which in turn serves as substrate for angiotensin converting enzyme (ACE) to form Ang II. The endogenous hormone Ang II is a linear octapeptide (Asp1-Arg2-Val3-Tyr4-Ile5-His6-Pro7-Phe8), and is an active component of the RAS.

The angiotensin II type 1 (AT1) receptor is expressed in most organs, and is believed to be responsible for the majority of the pathological effects of Ang II.

Several studies in adult individuals appear to demonstrate that, in the modulation of the response following Ang II stimulation, activation of the AT2 receptor has opposing effects to those mediated by the AT1 receptor.

The angiotensin II type 2 (AT2) receptor has also been shown to be involved in apoptosis and inhibition of cell proliferation (de Gasparo M et al. Pharmacol Rev 2000; 52:415-472).

More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339).

The expected pharmacological effects of agonism of the AT2 receptor are described in general in de Gasparo M et al., Pharmacol Rev 2000; 52:415-472. However, it is not mentioned that agonism of the AT2 receptor may be used for prevention or treatment of muscular dystrophy or complications associated therewith.

The effects of Ang II on cell growth, inflammation and extracellular matrix synthesis are mainly coupled to AT1, whereas the function of AT2 has been heavily investigated and new research indicates that it is more prevalent in damaged tissue and exerts reparative properties and properties opposing the AT1 receptor. The AT2 receptor has been shown to be important in reducing myocyte hypertrophy and potentially useful in treating idiopathic pulmonary fibrosis.

AT2 receptor agonists have also been described, for instance, in international patent application WO 2002/096883. However, these compounds were not suggested for prevention or treatment of muscular dystrophy or complications associated therewith.

The skilled person will understand that references to an AT2 receptor agonist include references to compounds that can bind to the AT2 receptor and induce a biological response from the AT2 receptor.

Thus, compounds of the invention include AT2 receptor agonists that fully activate and those that partially activate the AT2 receptor and those compounds that can stimulate or activate the AT2 receptor.

In some embodiments, an AT2 receptor agonist may be defined to include any compound that can stimulate or activate the AT2 receptor. In some embodiments, the compound of the invention is an AT2 receptor specific agonist that binds selectively to the AT2 receptor.

Particular compounds of the invention include N-butyloxycarbonyl-3-(4-imidazol-1-ylmethylphenyl)-5-iso-butyl-thiophene-2-sulfonamide (C21), or a pharmaceutically acceptable salt, solvate or prodrug thereof.

Particular compounds of the invention that bind selectively to the AT2 receptor include N-butyloxycarbonyl-3-(4-imidazol-1-ylmethylphenyl)-5-iso-butylthiophene-2-sulfonamide (C21).

The structure of N-butyloxycarbonyl-3-(4-imidazol-1-ylmethylphenyl)-5-iso-butylthiophene-2-sulfonamide (C21) is shown below.

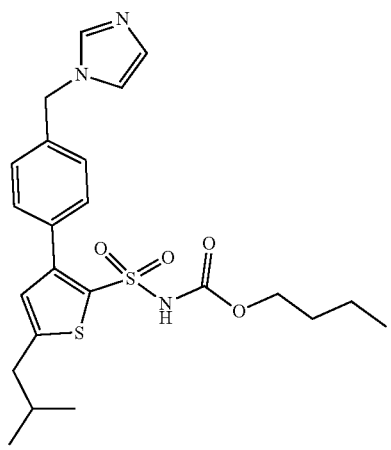 [SMILES: CCCCOC(=O)NS(=O)(=O)c1sc(CC(C)C)cc1-c1ccc(Cn2ccnc2)cc1]

N-butyloxycarbonyl-3-(4-imidazol-1-ylmethylphenyl)-5-iso-butylthiophene-2-sulfonamide (C21) may be made in accordance with techniques well known to those skilled in the art, for example as described in international patent application WO 2002/096883, all of its content hereby incorporated by reference.

Pharmaceutically-acceptable salts include, but are not limited to, acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example, using a suitable ion exchange resin. A particular salt of C21 that may be mentioned is the HCl salt. For the avoidance of doubt, other pharmaceutically acceptable derivatives of compounds of the invention are included within the scope of the invention (e.g. solvates, prodrugs etc).

As used herein, a "prodrug" is a substance that undergoes an in vivo modification when administered to a subject, wherein the product of the in vivo modification is a therapeutically effective compound of the invention. Prodrugs of compounds of the invention may be prepared by, for example, preparing a given compound of the invention as an ester. Thus, for example, an esterified form of the compound of the invention may be administered to a subject and may be de-esterified in vivo thereby releasing a therapeutically effective compound of the invention. Alternatively, some compounds may be prepared as prodrugs by adding short polypeptides (e.g., 1-6 amino acids) to the compound. Such prodrugs when administered to a subject may be cleaved (by, e.g., trypsin or other peptidases/proteases) thereby releasing a therapeutically effective compound of the invention. Formation of prodrugs is not limited by the specific examples described herein. Other ways of preparing therapeutically effective compounds as prodrugs are known to the person skilled in the art.

Compounds of the invention may exhibit tautomerism. All tautomeric forms and mixtures thereof are included within the scope of the invention.

Compounds of the invention also contain one or more asymmetric carbon atoms and may therefore exhibit optical and/or diastereoisomerism. Diastereoisomers may be separated using conventional techniques, e.g. chromatography or fractional crystallization. The various stereoisomers may be isolated by separation of a racemic or other mixture of the compounds using conventional, e.g. fractional crystallization or HPLC, techniques. Alternatively, the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

The compounds of the invention are useful because they possess pharmacological activity. In particular, the compounds of the invention are agonists of Ang II, more particularly, they are agonists of the AT2 receptor, and, especially, are selective agonists of that sub-receptor. Compounds of the invention have the advantage that they bind selectively to, and exhibit agonist activity at, the AT2 receptor. By compounds that "bind selectively" to the AT2 receptor, we include that the affinity ratio for the relevant compound (AT2:AT1) is at least 50:1, at least 100:1, preferably at least 1000:1, more preferably at least 10000:1, and even more preferably at least 25000:1.

The present inventors have found that the compounds of the invention (AT2 receptor agonists) are useful for the prevention and treatment of muscular dystrophy based on studies conducted in an established mouse model of LGMD. According to a further aspect of the present invention, there is provided a method for the prevention or treatment of muscular dystrophy or complications associated therewith, which method comprises administration of a therapeutically effective amount of a compound of the invention or a pharmaceutically acceptable salt thereof (e.g., an HCl salt of a compound of the invention), solvate or prodrug thereof to a subject in need thereof (i.e. a subject suffering from, or at risk of suffering from, such a condition).

Muscular dystrophies are a clinically and genetically heterogeneous group of diseases that are united by the presence of clinical features of muscle disease (primarily extremity muscle weakness and the disabilities resulting from it) and pathological presence of dystrophic muscle as defined by muscle biopsy features consistent with a dystrophy and/or significantly elevated serum creatine kinase levels. References herein to muscular dystrophy include references to all clinically recognized forms of muscular dystrophy, both collectively and individually. These include Duchenne muscular dystrophy, myotonic dystrophy, facioscapulohumeral muscular dystrophy, Becker muscular dystrophy, limb-girdle muscular dystrophy, oculopharyngeal muscular dystrophy, and Emery-Dreifuss muscular dystrophy. The compounds of the invention may therefore be used in the prevention or treatment of any of the above-mentioned diseases or complications associated therewith. Particular diseases that may be mentioned in this respect include Duchenne muscular dystrophy, which is the most common pediatric muscular dystrophy, and myotonic muscular dystrophy, which is the most common adult onset form (though it often presents in infancy and childhood). Another disease that may be mentioned in this respect is limb-girdle muscular dystrophy. Thus, in another embodiment, the methods and uses described herein may be used to treat or prevent limb-girdle muscular dystrophy, muscle weakness associated with limb-girdle muscular dystrophy or cardiopulmonary complications associated with limb-girdle muscular dystrophy.

Notable complications and symptoms associated with muscular dystrophy and which may be treated or prevented by the methods described herein include muscle weakness, progressive muscular wasting, muscle spasms, reduced ambulation, myopathic gait, poor balance, scoliosis, cardiomyopathy, cardiac disease, respiratory difficulty and respiratory disease. In subjects suffering from muscular dystrophy, the methods of the invention are particularly effective for preserving and/or improving muscle strength, as well as improving general locomotor activity, particularly ambulation. The methods are also effective in reducing the extent to which skeletal muscle fibrosis occurs in subjects suffering from or at risk of suffering from muscular dystrophy.

Treatment of subjects suffering from or at risk of suffering from muscular dystrophy with a compound of the invention may also help to reduce cardiac dysfunction and/or improves heart function, particularly cardiomyopathy (e.g. dilated cardiomyopathy).

Other complications may be associated with particular forms of muscular dystrophy, as will be known to those skilled in the art, and these may also be treated or prevented by the methods described herein. References herein to complications that are associated with muscular dystrophy include clinical complications and symptoms that arise directly from the existence of muscular dystrophy in a subject.

Subjects suitable to be treated with formulations of the present invention include, but are not limited to, mammalian subjects. In some embodiments, the subject can be a human subject, a rodent subject (such as a mouse, a rat, or a hamster), or a domesticated animal subject (such as a dog, a cat, a pig, cattle, a sheep, a goat, a chicken, or a rabbit). In more particular embodiments, the subject is a human.

The compounds of the invention will normally be administered orally, intravenously, subcutaneously, buccally, rectally, dermally, nasally, tracheally, bronchially, by any other parenteral route or via inhalation, in a pharmaceutically acceptable dosage form. Additional methods of administration include but are not limited to intraarterial administration, intramuscular administration, intraperitoneal administration, intraportal administration, intradermal administration, epidural administration, and/or intrathecal administration. Particular routes of administration that may be mentioned include nasal, oral and parenteral administration.

The compounds of the invention may be administered alone, but are preferably administered by way of known pharmaceutical formulations, including tablets (e.g. tablets for oral administration), capsules (e.g. capsules for oral administration), elixirs (e.g. elixirs for oral administration), suppositories (e.g. suppositories for rectal administration), sterile solutions (e.g. sterile solutions for parenteral administration or sterile solutions for intramuscular administration), or sterile suspensions (e.g. sterile suspensions for parenteral administration or sterile suspensions intramuscular administration), and the like.

Such formulations may be prepared in accordance with standard and/or accepted pharmaceutical practice.

The formulations may conveniently be presented in unit dosage form and may be prepared by any of the methods well known in the art of pharmacy. Such methods include the step of bringing into association the molecule with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In addition to the ingredients particularly mentioned above, the formulations may include other agents conventional in the art having regard to the type of formulation in question, for example those suitable for oral administration may include flavouring agents.

According to a further aspect of the invention there is thus provided a pharmaceutical formulation comprising a compound of the invention, in admixture with a pharmaceutically acceptable adjuvant, diluent or carrier, for use in the prevention or treatment of muscular dystrophy or complications associated with muscular dystrophy.

Acceptable carriers and diluents for therapeutic use are well known in the pharmaceutical art, and are described, for example, in Remington's Pharmaceutical Sciences, Mack Publishing Co. (A. R. Gennaro ed. 1985). The choice of pharmaceutical carriers and diluents can be selected with regard to the intended route of administration and standard pharmaceutical practice. The pharmaceutical formulations may comprise as, or in addition to, the carriers and diluents any suitable binder, lubricant, suspending agent, coating agent, or solubilizing agent. Preservatives, stabilizers, dyes and even flavoring agents may be provided in the pharmaceutical formulation.

Compounds of the invention may also be administered in combination with one or more other AT2 agonists that are known in the art, or alternatively in combination with one or more AT1 receptor antagonists (antagonists of the angiotensin II type 1 receptor) that are known in the art, such as losartan or candesartan, and/or in combination with an inhibitor of angiotensin converting enzyme (ACE), such as enalapril or ramipril. Such combinations may therefore be useful for the prevention or treatment of muscular dystrophy or complications associated with muscular dystrophy.

AT1 receptor antagonists that are known in the art and that may be used in combination with the compounds of the invention include losartan, azilsartan, candesartan, eprosartan, fimasartan, irbesartan, milfasartan, olmesartan, pomisartan, pratosartan, ripiasartan, saprisartan, tasosartan, telmisartan, valsartan and combinations thereof.

ACE inhibitors that are known in the art and that may be used in combination with the compounds of the invention include captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and combinations thereof.

According to a further aspect of the invention, there is provided a combination product comprising:

(A) an AT2 receptor agonist or a compound that stimulates AT2 receptors, and (B) an AT1 receptor antagonist, and/or an ACE inhibitor, wherein each of components (A) and (B) is formulated in admixture with a pharmaceutically-acceptable adjuvant, diluent or carrier, for use in the prevention or treatment of muscular dystrophy or complications associated with muscular dystrophy. Such combination products enable the administration of an AT2 receptor agonist or a compound that stimulates an AT2 receptor (as defined herein), in conjunction with an AT1 receptor antagonist and/or an ACE inhibitor, and each component may be presented either in separate formulations, wherein at least one of those formulations comprises an AT2 receptor agonist or a compound that stimulates an AT2 receptor (as defined herein, e.g., a compound of the invention, or a pharmaceutically acceptable salt, solvate or prodrug thereof), and at least one formulation comprises an AT1 receptor antagonist and/or an ACE inhibitor, or may be presented (i.e., formulated) as a combined preparation (i.e., presented as a single formulation including an AT2 receptor agonist or a compound that stimulates an AT2 receptor together with either an AT1 receptor antagonist and/or an ACE inhibitor). In some embodiments, the AT2 receptor agonist is provided in the same composition or pharmaceutical formulation as the AT1 receptor antagonist and/or the ACE inhibitor. In some embodiments, AT2 receptor agonist is provided in a separate formulation from the AT1 receptor antagonist and/or the ACE inhibitor and the separate formulations are administered to the subject simultaneously, sequentially or separately.

Thus, there is further provided:

(1) a pharmaceutical formulation comprising an AT2 receptor agonist or a compound that stimulates an AT2 receptor (e.g., a compound of the invention, or a pharmaceutically acceptable salt, solvate or prodrug thereof) and an AT1 receptor antagonist and/or an ACE inhibitor, in admixture with a pharmaceutically-acceptable adjuvant, diluent and/or carrier, for use in preventing or treating muscular dystrophy or complications associated with muscular dystrophy; and (2) a kit of parts comprising components:

(a) a pharmaceutical formulation comprising an AT2 receptor agonist or a compound that stimulates an AT2 receptor (e.g., a compound of the invention, or a pharmaceutically acceptable salt, solvate or prodrug thereof), in admixture with a pharmaceutically-acceptable adjuvant, diluent and/or carrier; and (b) a pharmaceutical formulation including an AT1 receptor antagonist and/or an ACE inhibitor, in admixture with a pharmaceutically-acceptable adjuvant, diluent and/or carrier, which components (a) and (b) are each provided in a form that is suitable for administration in conjunction with the other, for use in preventing or treating muscular dystrophy or complications associated with muscular dystrophy. In some embodiments, the kit of parts further comprises instructions for using said pharmaceutical formulation comprising an AT2 receptor agonist in the prevention or treatment of muscular dystrophy. In a further preferred embodiment, the AT2 receptor agonist is C21 or a pharmaceutically acceptable salt, solvate or prodrug thereof.

In an embodiment, a pharmaceutical formulation is provided comprising a compound of the invention, or a pharmaceutically acceptable salt, solvate or prodrug thereof, and an AT1 receptor antagonist, in admixture with a pharmaceutically-acceptable adjuvant, diluent or carrier, for use in preventing or treating muscular dystrophy or complications associated with muscular dystrophy.

In an embodiment, a kit of parts is provided comprising components:

(a) a pharmaceutical formulation including a compound of the invention or a pharmaceutically acceptable salt, solvate or prodrug thereof, in admixture with a pharmaceutically-acceptable adjuvant, diluent or carrier; and (b) a pharmaceutical formulation including an AT1 receptor antagonist, in admixture with a pharmaceutically-acceptable adjuvant, diluent or carrier, which components (a) and (b) are each provided in a form that is suitable for administration in conjunction with the other, for use in preventing or treating muscular dystrophy or complications associated with muscular dystrophy.

In an embodiment, a pharmaceutical formulation is provided comprising a compound of the invention, or a pharmaceutically acceptable salt, solvate or prodrug thereof, and an angiotensin converting enzyme inhibitor, in admixture with a pharmaceutically-acceptable adjuvant, diluent or carrier, for use in preventing or treating muscular dystrophy or complications associated with muscular dystrophy.

In an embodiment, a kit of parts is provided comprising components:

(a) a pharmaceutical formulation including a compound of the invention or a pharmaceutically acceptable salt, solvate or prodrug thereof, in admixture with a pharmaceutically-acceptable adjuvant, diluent or carrier; and (b) a pharmaceutical formulation including an angiotensin converting enzyme inhibitor, in admixture with a pharmaceutically-acceptable adjuvant, diluent or carrier, which components (a) and (b) are each provided in a form that is suitable for administration in conjunction with the other, for use in preventing or treating muscular dystrophy or complications associated with muscular dystrophy.

Depending upon the subject to be treated and the route of administration, the compounds of the invention may be administered at varying doses. Although doses will vary from subject to subject, suitable daily doses are in the range of about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein) per subject, administered in single or multiple doses. More preferred daily doses are in the range 2.5 to 250 mg (e.g., about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg and the like or any range or value therein) per subject.

Individual doses of compounds of the invention may be in the range 1 to 100 mg (e.g., about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, and the like, or any range or values therein). Advantageously, compounds of the present invention may be administered in single doses, e.g. once daily or more seldom, or in a total daily dosage administered in divided doses of two, three or four times daily.

In any event, the physician, or the skilled person, will be able to determine the actual dosage which will be most suitable for an individual subject, which is likely to vary with the condition that is to be treated, as well as the age, weight, sex and response of the particular subject to be treated. The above-mentioned dosages are exemplary of the average case; there can, of course, be individual instances where higher or lower dosage ranges are merited, and such are within the scope of this invention.

In a particular embodiment, the compounds of the present invention may be administered over a period of at least two days; for example, at least three days, or at least four days, or at least five days, or at least six days, or at least seven days (i.e. one week), or at least eight days, or at least nine days, or at least ten days, or at least 11 days, or at least 12 days, or at least 13 days, or at least 14 days (i.e. two weeks), or at least three weeks, or at least four weeks, or at least one month, or at least five weeks, or at least six weeks, or at least seven weeks, or at least eight weeks, or at least two months, or at least three months, or at least four months, or at least five months, or at least six months, or at least seven months, or at least eight months, or at least nine months, or at least ten months, or at least 11 months, or at least 12 months (i.e. one year), or at least two years, or at least three years, or at least four years, or at least five years, or at least six years, or at least seven years, or at least eight years, or at least nine years, or at least ten years, or at least 11 years, or at least 12 years, or at least 13 years, or at least 14 years, or at least 15 years, or at least 16 years, or at least 17 years, or at least 18 years, or at least 19 years, or at least 20 years, or at least 25 years, or at least 30 years, or at least 35 years, or at least 40 years, or at least 45 years, or at least 50 years.

The compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties than compounds known in the prior art. Such effects may be evaluated clinically, objectively and/or subjectively by a health care professional, a treatment subject or an observer.

In one aspect of the invention, a compound of the invention may have an anti-fibrotic effect, with reduction of fibrosis and prevention of further deposition of extra cellular matrix.

Figure 3:
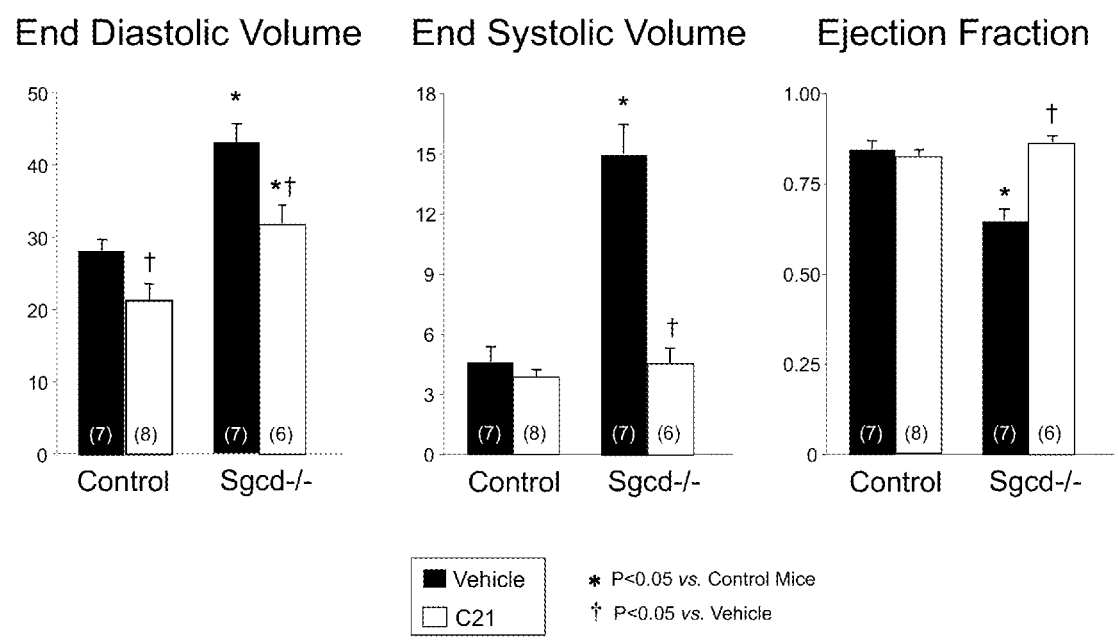
FIG. 3 shows the effects of C21 on cardiac function compared to control in a δSgcd/− mouse model.

In one aspect of the invention, administration of a compound of the invention can improve cardiac dysfunction and improve heart function measured as ejection fraction and end diastolic volume and end systolic volume in a subject suffering from muscular dystrophy (FIG. 3).

In a related aspect of the invention, administration of a compound of the invention can increase baroreflex sensitivity and vagal tone, as well as decrease sympathetic tone compared to placebo (FIG. 1).

Figure 2:
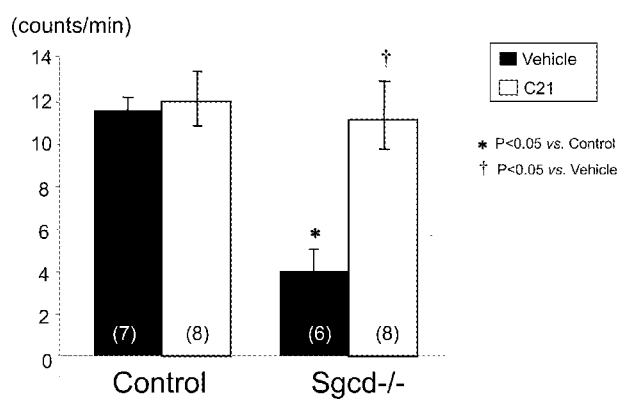
FIG. 2 shows the effects of C21 on spontaneous locomotor activity compared to control in a δSgcd−/− mouse model.

In another aspect of the invention, administration of a compound of the invention can increase spontaneous locomotor activity to levels comparative with controls (FIG. 2).

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

The effect of C21 was evaluated in a δSgcd–/– mouse model, which is a genetically modified model to imitate limb-girdle muscular dystrophy (LGMD). At 3 weeks of age, δSgcd–/– mice and control mice were administrated C21 (0.03 mg/kg/day, osmotic minipump, SC) or vehicle for eight weeks. Data from conscious mice were collected during the last week of treatment. At the end of the experiment, tissues were harvested for histopathology and molecular gene expression measurements.

A radiotelemetry probe (PC10-DSI) that enabled measurement of arterial blood pressure (BP), heart rate (HR) and locomotor activity was inserted into the thoracic aorta through the left common carotid artery under 2% isoflurane anesthesia when the mice were 9 weeks of age. When the mice reached 11-12 weeks of age, changes in BP, HR, and locomotor activity were measured over a minimum of 24 hours at a sampling rate of 500 Hz. In addition, BP was continuously recorded at a high sampling frequency of 2000 Hz for 1-2 hours, to collect data for assessment of spontaneous baroreflex sensitivity (sequence technique), sympathetic tone (HR changes with propranolol) and vagal tone (HR changes with methylatropine).

The Sgcd–/– genetic modification in mice had a significant impact on autonomic functions including decreased baroreflex sensitivity and vagal tone and increased sympathetic tone compared to control mice. Administration of C21 to Sgcd–/– mice resulted in an increase in baroreflex sensitivity and vagal tone and decreased sympathetic tone compared to sgcd–/– placebo treated mice (FIG. 1).

Furthermore, sgcd–/– mice had decreased spontaneous locomotor activity compared to control animals. In these animals, administration of C21 increased the spontaneous locomotor activity to levels comparative to control animals (FIG. 2).

In addition, older-aged sgcd–/– mice exhibited impaired cardiac function measured as end diastolic volume, end systolic volume and ejection fraction, compared to control mice. Administration to C21 improved the cardiac function (FIG. 3).

Echocardiography was performed in telemeter-implanted mice using Philips Sonos 5500 clinical imager in mice sedated with midazolam.

What is claimed is:

1. A method of treating muscular dystrophy or complications associated with muscular dystrophy in a subject in need thereof, comprising administering to the subject a therapeutically effective amount of an AT2 receptor agonist or a pharmaceutically acceptable salt, solvate or prodrug thereof, wherein the muscular dystrophy is selected from the group consisting of Duchenne muscular dystrophy, myotonic dystrophy, facioscapulohumeral muscular dystrophy, Becker muscular dystrophy, limb-girdle muscular dystrophy, oculopharyngeal muscular dystrophy, and Emery-Dreifuss muscular dystrophy, wherein the AT2 receptor agonist is N-butyloxycarbonyl-3-(4-imidazol-1-ylmethylphenyl)-5-iso-butylthiophene-2-sulfonamide (C21).

2. The method according to claim 1, wherein the AT2 receptor agonist is a selective agonist of an AT2 receptor.

3. The method of claim 2, wherein the selective agonist of an AT2 receptor is a non-peptide selective agonist.

4. The method of claim 3, wherein the AT2 receptor agonist is an HCl salt.

5. The method of claim 1 wherein the muscular dystrophy is Duchenne muscular dystrophy, myotonic dystrophy, or limb-girdle muscular dystrophy.

6. The method of claim 1, wherein the method treats one or more complications associated with muscular dystrophy selected from the group consisting of: muscle weakness, progressive muscular wasting, muscle spasms, reduced ambulation, myopathic gait, poor balance, scoliosis, cardiomyopathy, cardiac disease, respiratory difficulty and respiratory disease.

7. The method of claim 1, wherein the method reduces cardiac dysfunction and/or improves heart function in a subject suffering from muscular dystrophy.

8. The method of claim 1, wherein the method treats limb-girdle muscular dystrophy, muscle weakness associated with limb-girdle muscular dystrophy or cardiopulmonary complications associated with limb-girdle muscular dystrophy.

9. The method of claim 1, wherein the administration comprises the introduction of the AT2 receptor agonist, or pharmaceutically acceptable salt, solvate or prodrug thereof, into the subject nasally, orally, or parenterally.

10. The method of claim 1, wherein the AT2 receptor agonist, or pharmaceutically acceptable salt, solvate or prodrug thereof, is administered to a subject at a dose of from about 1 to about 1000 mg per day.

11. The method of claim 1, wherein the AT2 receptor agonist, or pharmaceutically acceptable salt, solvate or prodrug thereof, is administered in combination with an AT1 receptor antagonist.

12. The method of claim 11, wherein the AT1 receptor antagonist is selected from the group consisting of: losartan, azilsartan, candesartan, eprosartan, fimasartan, irbesartan, milfasartan, olmesartan, pomisartan, pratosartan, ripiasartan, saprisartan, tasosartan, telmisartan, valsartan and combinations thereof.

13. The method of claim 1, wherein the AT2 receptor agonist, or pharmaceutically acceptable salt, solvate or prodrug thereof, is administered in combination with an inhibitor of angiotensin converting enzyme (ACE).

14. The method of claim 13, wherein the angiotensin converting enzyme (ACE) inhibitor is selected from the group consisting of: captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and combinations thereof.

15. A composition for the treatment of muscular dystrophy or complications associated with muscular dystrophy comprising: an AT2 receptor agonist, or a pharmaceutically acceptable salt, solvate or prodrug thereof, wherein the AT2 receptor agonist is N-butyloxycarbonyl-3-(4-imidazol-1-ylmethylphenyl)-5-iso-butylthiophene-2-sulfonamide (C21), and further comprising an AT1 receptor antagonist and/or an inhibitor of angiotensin converting enzyme (ACE), wherein the muscular dystrophy is selected from the group consisting of Duchenne muscular dystrophy, myotonic dystrophy, facioscapulohumeral muscular dystrophy, Becker muscular dystrophy, limb-girdle muscular dystrophy, oculopharyngeal muscular dystrophy, and Emery-Dreifuss muscular dystrophy.

16. The composition of claim 15, wherein the composition comprises an AT1 receptor antagonist.

17. The composition of claim 16, wherein the composition comprises an inhibitor of ACE.

18. The composition of claim 17, wherein the AT2 receptor agonist is an HCl salt.

19. A method for treating muscular dystrophy in a subject in need thereof comprising administering to the subject a composition comprising an AT2 receptor agonist, wherein the AT2 receptor agonist is N-butyloxycarbonyl-3-(4-imidazol-1-ylmethylphenyl)-5-iso-butylthiophene-2-sulfonamide (C21) or a pharmaceutically acceptable salt (preferably an HCl salt), a solvate or a prodrug thereof.

20. The method of claim 19, wherein the muscular dystrophy is selected from the group consisting of Duchenne muscular dystrophy, myotonic dystrophy, facioscapulohumeral muscular dystrophy, Becker muscular dystrophy, limb-girdle muscular dystrophy, oculopharyngeal muscular dystrophy, and Emery-Dreifuss muscular dystrophy.

* * * * *